(12) United States Patent
Benzon

(10) Patent No.: US 9,072,567 B2
(45) Date of Patent: Jul. 7, 2015

(54) SUPERSTRUCTURE AND METHODS FOR MANUFACTURING THE SAME

(71) Applicant: Heraeus Dental AB, Helsingborg (SE)

(72) Inventor: Sture Benzon, Hoganas (SE)

(73) Assignee: Heraeus Kulzer Nordic AB, Helsingborg (SE)

(*) Notice: Subject to any disclaimer, the term of this patent is extended or adjusted under 35 U.S.C. 154(b) by 0 days.

(21) Appl. No.: 13/935,677

(22) Filed: Jul. 5, 2013

(65) Prior Publication Data
US 2014/0017631 A1  Jan. 16, 2014

(30) Foreign Application Priority Data
Jul. 11, 2012 (SE) .................................. 1250815

(51) Int. Cl.
*A61C 8/00* (2006.01)
(52) U.S. Cl.
CPC .............. *A61C 8/0053* (2013.01); *A61C 8/0054* (2013.01); *A61C 8/0068* (2013.01); *A61C 8/0048* (2013.01)
(58) Field of Classification Search
CPC ........ A61C 8/48; A61C 13/273; A61C 8/005; A61C 8/0053–8/0072
USPC ........................ 433/172–176, 201.1, 167, 190
See application file for complete search history.

(56) References Cited

U.S. PATENT DOCUMENTS

| | | | | |
|---|---|---|---|---|
| 2,599,044 A | * | 6/1952 | Brennan | 433/173 |
| 3,618,212 A | * | 11/1971 | Weissman | 433/174 |
| 3,732,621 A | * | 5/1973 | Bostrom | 433/174 |
| 4,850,869 A | * | 7/1989 | Steinfort et al. | 433/172 |
| 4,881,897 A | * | 11/1989 | Franek et al. | 433/169 |
| 4,932,868 A | * | 6/1990 | Linkow et al. | 433/174 |
| 4,955,811 A | * | 9/1990 | Lazzara et al. | 433/173 |
| 5,071,350 A | * | 12/1991 | Niznick | 433/173 |
| 5,073,110 A | * | 12/1991 | Barbone | 433/173 |
| 5,092,770 A | * | 3/1992 | Zakula | 433/172 |
| 5,106,299 A | * | 4/1992 | Ghalili | 433/172 |
| 5,116,225 A | * | 5/1992 | Riera | 433/173 |
| 5,125,839 A | * | 6/1992 | Ingber et al. | 433/169 |
| 5,133,662 A | * | 7/1992 | Metcalfe | 433/169 |
| 5,480,304 A | * | 1/1996 | Nardi | 433/172 |
| 5,520,540 A | * | 5/1996 | Nardi et al. | 433/172 |

(Continued)

FOREIGN PATENT DOCUMENTS

WO   WO 01/70127   9/2001

*Primary Examiner* — Cris L Rodriguez
*Assistant Examiner* — Hao D Mai
(74) *Attorney, Agent, or Firm* — Merchant & Gould P.C.

(57) ABSTRACT

A dental superstructure attaching system for use with a dental implant includes a longitudinal member being connectable with an implant or an implant connecting member via an at least partially curved interface area. The longitudinal member includes a main member forming the lingual part of said longitudinal member, and a lever member forming the buccal or labial part of said longitudinal member. The longitudinal member includes means for urging said lever member and said main member away from each other, such that said longitudinal member is secured to said implant or implant connecting member. The system includes a casing (200) for attachment to a dental superstructure on the outer surface of the casing (200), said casing (200) having a cavity (201) for housing the longitudinal member (102), such that when urging said lever member (102b) and said main member (102a) away from each other, the longitudinal member (102) is secured in said cavity (201).

9 Claims, 4 Drawing Sheets

(56) References Cited

U.S. PATENT DOCUMENTS

| | | | |
|---|---|---|---|
| 5,527,182 A | 6/1996 | Willoughby | |
| 5,842,864 A * | 12/1998 | Unger | 433/172 |
| 5,967,781 A * | 10/1999 | Gittleman | 433/172 |
| 5,997,299 A * | 12/1999 | Unger | 433/173 |
| 6,843,653 B2 * | 1/2005 | Carlton | 433/174 |
| 7,435,088 B2 * | 10/2008 | Brajnovic | 433/173 |
| 8,303,303 B2 * | 11/2012 | Brajnovic | 433/75 |
| 8,348,668 B2 * | 1/2013 | Lauridsen et al. | 433/173 |

\* cited by examiner

SUPERSTRUCTURE AND METHODS FOR MANUFACTURING THE SAME

This application claims benefit of Ser. No. 1250815-6, filed Jul. 11, 2012 in Sweden and which application is incorporated herein by reference. To the extent appropriate, a claim of priority is made to the above disclosed application.

TECHNICAL FIELD

The present invention pertains to a dental superstructure attaching system for use with a dental implant. More specifically the present invention pertains to a system to be arranged in between a dental implant and a dental superstructure/framework, members thereof, and methods for attaching a dental superstructure to a dental implant via such a system.

BACKGROUND

The goal of a dental implant system is to restore the patient to normal function, comfort, aesthetic, speech and health regardless of the current oral condition. These implant systems are based on the implantation of dental implants, such as dental implants made of biocompatible titanium, through insertion into the patient's jawbone. In this respect, the use of biocompatible titanium started in Sweden as early as 1950, and has since then been further developed and spread worldwide. During the 1980's a number of implant systems entered the world market.

When securing a dental prosthesis to the jaw of a patient, it is commonly known to attach a superstructure to osseointegrated dental implants. However, since the position and angle of the dental implants vary greatly from patient to patient, the use of angled distances is common. These distances are placed upon the dental implant, and the superstructure is then most often cemented to the distances, since it is difficult to retain the superstructure to such distances by means of screws. However, when using separate distances, these will inevitably extend—at least to some extent—in the axial direction of the dental implant. It is then often very difficult or even impossible to apply the superstructure on such distances, since the application of the superstructure calls for a substantially parallel arrangement of the distances. Also, the mounting process when using such distances is very complicated and cumbersome, since a vast number of different distances must be tested on the implants, to find the needed match. Also, interfaces between the distances and the superstructure are hygienically bad.

WO01/70127 describes an arrangement comprising a spacer element for an implant. The spacer implant has a screw bore at a fixed angle relative the longitudinal axis of the implant, such that a holder configured to support a superstructure may be mounted in said screw bore at the corresponding angle. Hence, using this kind of system the mouth of the connection channel between the superstructure and the spacer element may be arranged with a freedom of choice in accordance with the angle of the screw bore of the spacer element.

However, the freedom of the above described system is limited to the predetermined angle of the spacer element, and the system requires specially adapted tools for assembling the arrangement.

Thus, there is a need for a new device and method allowing for improved construction of angled distances.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a method and a device according to the appended patent claims.

An object of the present invention is to provide a system for allowing a superstructure to be connected to said system without any visible attachment means.

A further object of the present invention is to provide a single system which may be connected to a dental implant at various angles.

A yet further object of the present invention is to provide a system allowing the superstructure to be connected to said system by means of a standard screw.

A still further object of the present invention is to provide a system allowing for an improved fit between the system and the superstructure/framework, and to also provide a system allowing for a variety of possible materials for manufacturing the superstructure/framework.

The general solution according to the invention is a two part superstructure attachment system forming a distance to be connected to a superstructure, which distance is angularly displaceable relative an implant and securable to said implant by a clamping effect caused by relative movement between the two parts, which in turn cooperates with a casing to be attached to the superstructure/framework.

In an aspect of the invention there is thus provided a dental superstructure attaching system for use with a dental implant, comprising a longitudinal member being connectable with an implant or an implant connecting member via an at least partially curved interface area, said longitudinal member comprising a main member and a lever member, wherein said longitudinal member further comprises means for urging said lever member and said main member away from each other, such that said longitudinal member is secured to said implant or implant connecting member, and a casing for attachment to a dental superstructure on the outer surface of the casing, said casing comprising a cavity for housing the longitudinal member, such that when urging said lever member and said main member away from each other, the longitudinal member is secured in said cavity.

In another aspect of the invention there is provided a method for attaching a dental superstructure to a dental implant, comprising the steps of: mounting an implant connecting member to said implant, said implant connecting member having an at least partially curved area at its distal end, providing a longitudinal member having a proximal end engageable with the shape of the distal end of said implant connecting member, said longitudinal member comprising a main member, and a lever member, arranging a dental superstructure onto said longitudinal member, arranging a casing, comprising a cavity for housing the longitudinal member, in or onto a dental superstructure, and securing said casing to said longitudinal member by urging said lever member and said main member away from each other.

In another aspect of the invention there is provided a method for attaching a dental superstructure to a dental implant having at least partially curved area at its distal end, comprising the steps of: providing a longitudinal member having a proximal end engageable with the shape of the distal end of said implant connecting member, said longitudinal member comprising a main member and a lever member, and arranging a dental superstructure onto said longitudinal member, arranging a casing, comprising a cavity for housing the longitudinal member, in or onto a dental superstructure, and securing said casing to said longitudinal member by urging said lever member and said main member away from each other.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

In general, the present invention pertains to a system and devices thereof, for obtaining a dental superstructure, and subsequently a dental prosthesis, comprising said dental superstructure and an appropriate facing material thereon, without any form of screw channel mouth in the masticating surface. The system instead assures that the superstructure may be attached to a dental implant through a tightening screw lingually. In this way a more aesthetic and endurable construction may be obtained.

Figure 1:
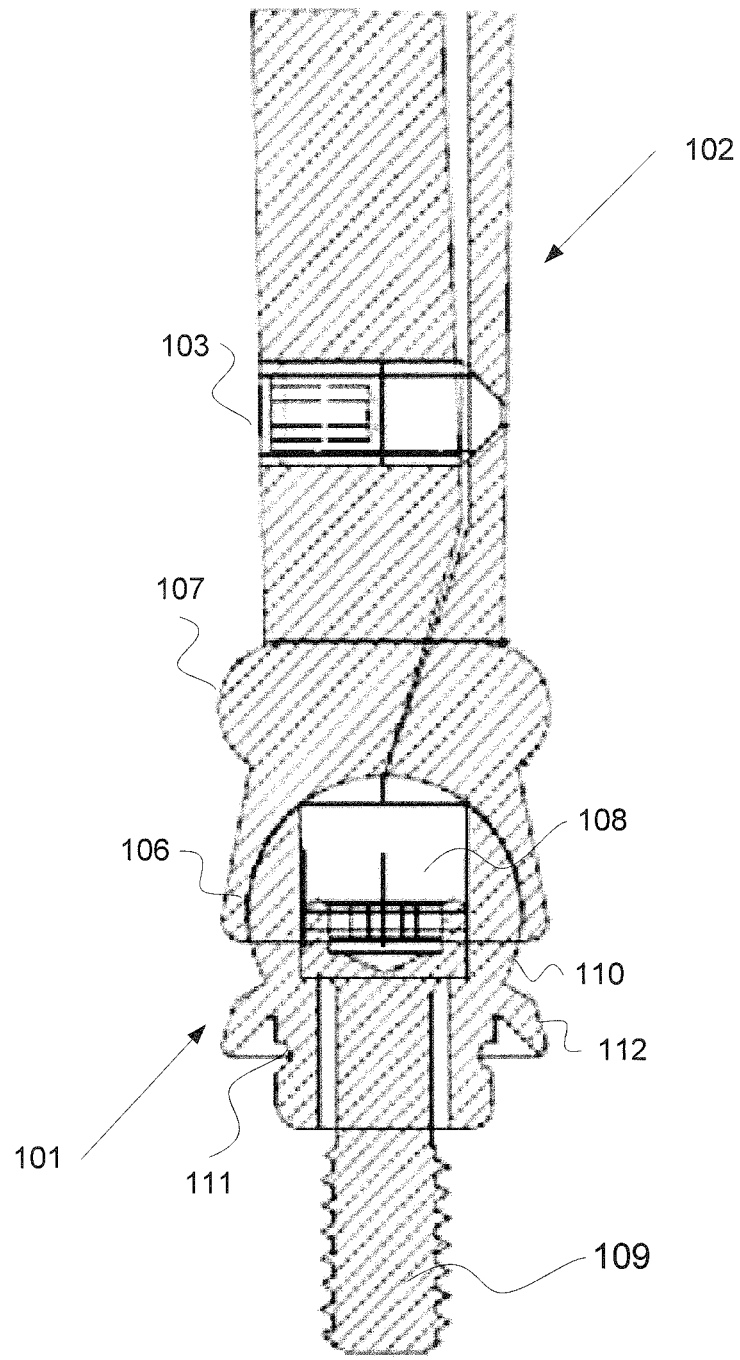
FIG. 1 is a schematic cross-section of a system according to an embodiment.
Figure 2:
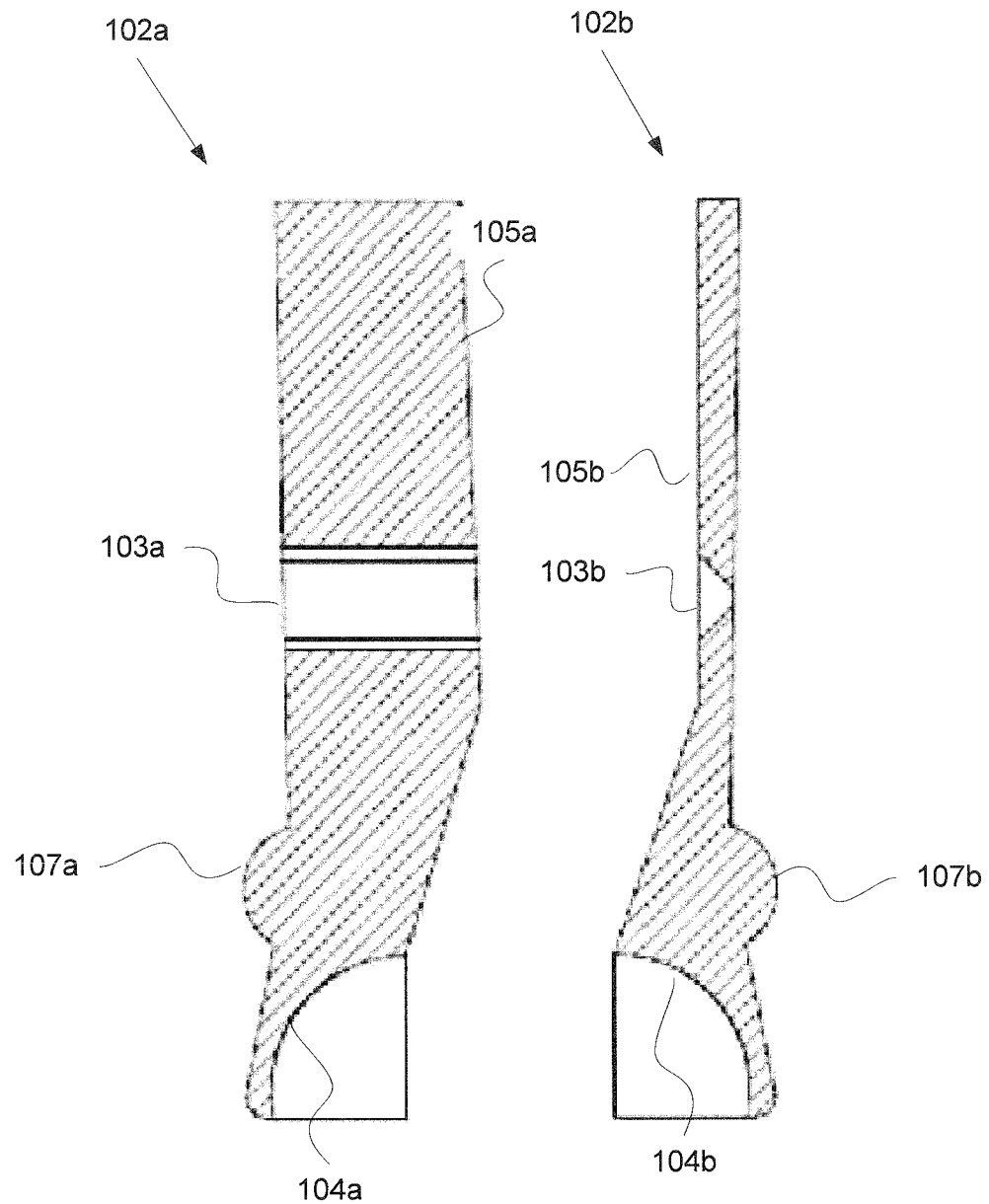
FIG. 2 is a schematic cross-section of a longitudinal member of the system shown in FIG. 1.

According to the embodiment in FIG. 1 and FIG. 2, a dental implant connecting member 101 and a longitudinal member 102 are disclosed. The dental implant connecting member 101 and the longitudinal member 102 are parts of a superstructure attachment system, said system comprising the dental implant connecting member 101, the longitudinal member 102, and a casing 200, according to FIGS. 3 and 4. The longitudinal member 102 is adapted to be inserted into a casing 200, in accordance with FIGS. 3 and 4, which will be further described below, which in turn is connected to a dental superstructure. The longitudinal member 102 comprises two portions, a main member 102a and a lever member 102b, which in use are held together by a screw member arranged in a correspondingly threaded screw hole 103. The two members 102a, 102b have a substantially longitudinal extension, and are intended to extend distally from the implant connecting part 101, and therefore also distally from the jaw bone to which an implant (not shown) is secured. The screw hole 103 extends substantially transversely in respect of the longitudinal extension of the two members 102a, 102b, and runs at least through portion 102a.

The thread of the screw hole 103 may be such that at least a part of the screw hole 103a in portion 102a is threaded. Portion 102b may comprise a receiving seat 103b, for receiving the screw member arranged in the screw hole 103a and protruding from an interface surface 105a on the portion 102a. In this way, the portion 102a may be pushed away from the portion 102b by screwing the screw member into the screw hole 103 and pushing onto the receiving seat 103b. The portion 102b may also have a threaded part in the receiving seat 103b. In this way the screw member may be prearranged in the screw hole, holding portion 102a and 102b together during application of the casing 200 thereon. The thread of the screw hole part in portion 102b may be threaded in the opposite direction to the thread in the screw hole 103a of portion 102a. In this way the separation action between portion 102a and 102b may be amplified, such that portion 102a and 102b are separated by two thread heights during every rotation of the screw member arranged in the screw hole 103.

The implant connecting member 101 and the longitudinal member 102 are connected to each other at a curved interface area 106 forming a ball-socket joint. The ball-socket joint is formed by a partially spherically shaped protrusion 110 arranged at the distal end of the dental implant member 101, and a recess 104a, 104b having a corresponding inverted shape and configured to engage with said protrusion 110.

Figure 3:
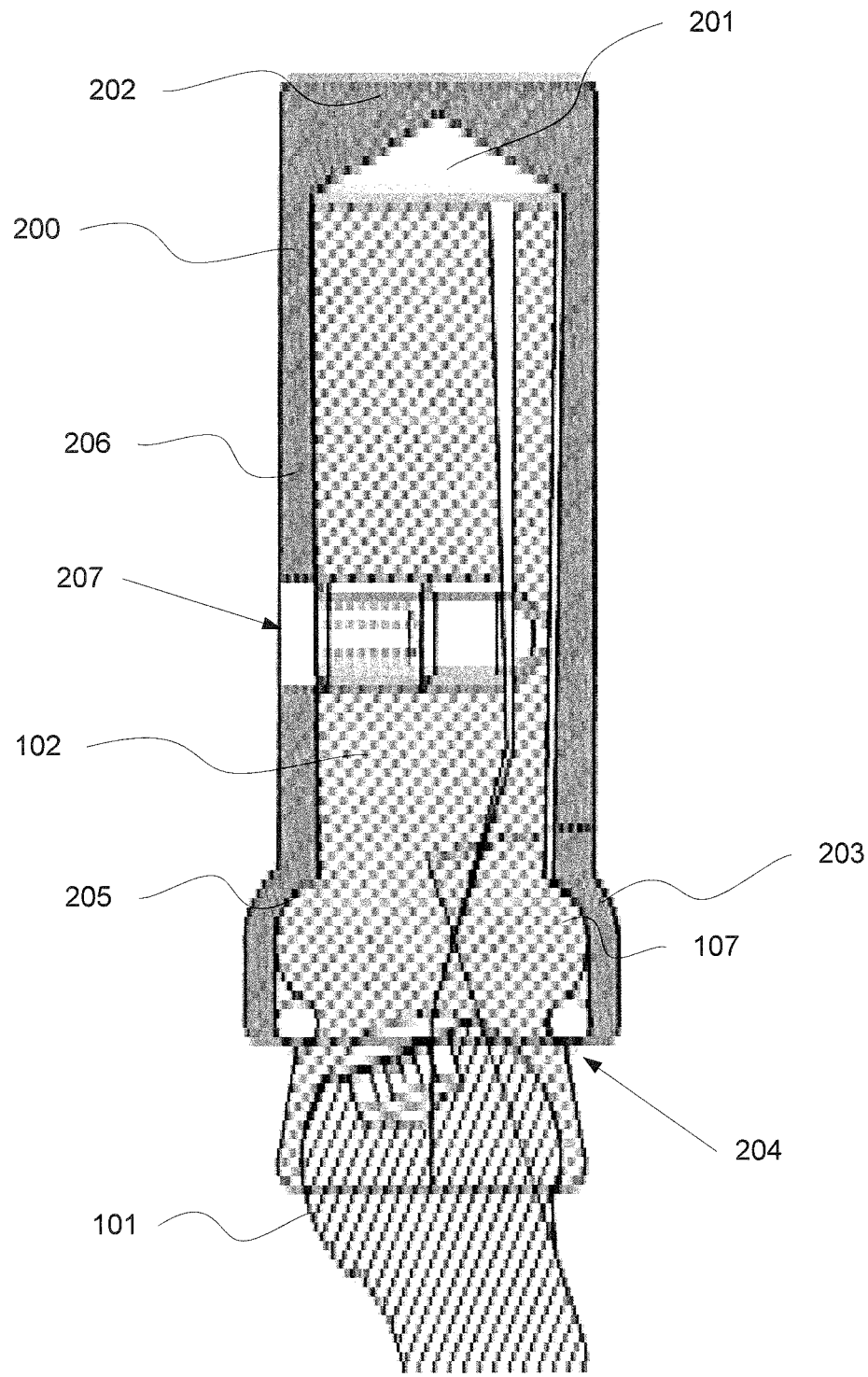
FIG. 3 is a schematic cross-section of a casing according to an embodiment, housing a longitudinal member according to FIGS. 1 and 2 therein.
Figure 4:
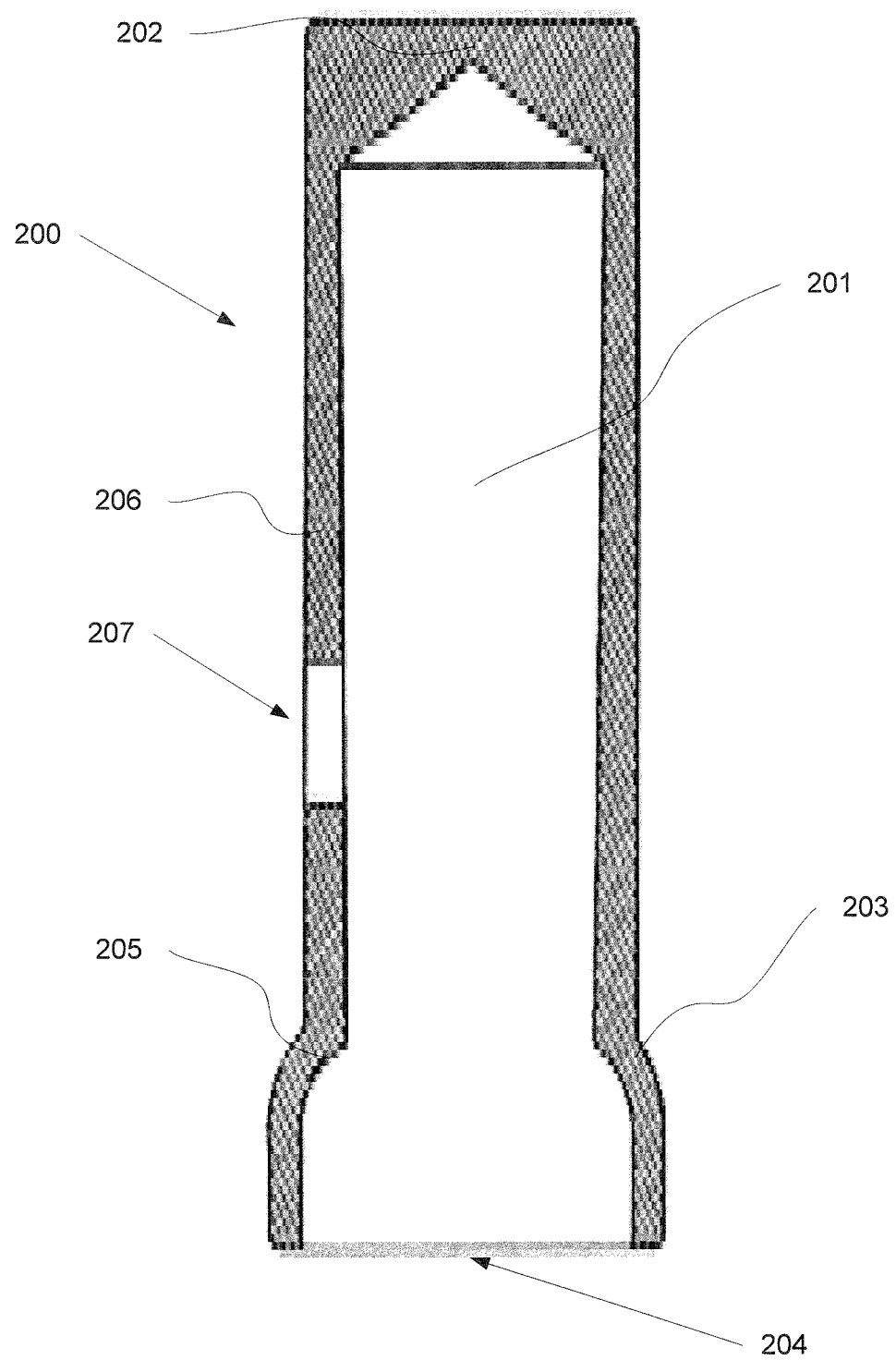
FIG. 4 is a schematic cross-section of a casing according to FIG. 3.

In FIGS. 3 and 4, a casing 200 is disclosed, in accordance with one embodiment of the invention. The casing 200 is to be inserted into a cavity in a dental superstructure. In this way, the dental superstructure can be provided with a predetermined cavity for receiving the casing 200, which cavity has a shape and size being known to for example the CAD/CAM equipment milling or shaping the dental superstructure. Within the casing 200 the longitudinal member 102 is intended to be received. In this way, the casing 200 may be manufactured in material being more resistant to strain and stress than the material of the dental superstructure. For example the casing 200 may be manufactured in stainless steel, titanium, CoCr etc., making it possible to manufacture the dental superstructure in more fragile materials, such as plastics. The casing 200 is substantially cylindrical, with a tubular cavity 201, extending into the casing 200 from the proximal end thereof. The distal end of the casing 200 is preferably closed, such that the cavity 201 ends in a distal bottom end wall 202. The cavity is adapted in size and shape to receive the longitudinal member 102.

The casing 200 is provided with a proximal outer shoulder 203. In this way—since the dental superstructure is manufactured and shaped to correspond to this exact cavity—the dental superstructure may bear upon the outer shoulder 203, which will facilitate arrangement and fixation of the casing into the dental superstructure and also distribute tensions and stresses between several cavity/casing positions in one dental superstructure, once the dental superstructure has been fixated to the dental implant, in accordance with below.

In the proximal end of, i.e. at the opening 204 of, the cavity 201 a ledge 205 is formed. The ledge 205 is adapted in size and shape to correspond to the flange 107 of the longitudinal member 102. The interaction between the ledge 201 and the flange 107 creates a pivot point for said lever member 102b. Since the casing 200 has a predetermined shape corresponding to the longitudinal member 102, the cooperation between the flange 107 and the ledge 205 may be close, to minimize movement and play between the two.

The casing 200 has a tubular wall 206, in accordance with above. The tubular wall 206 is provided with a through hole 207. The through hole 207 communicates with said cavity 201. The position of the through hole 207 corresponds in position to the through hole 103a of said main member 102a. The through hole 207 is also positioned distally of the proximal outer shoulder 203 and distally of the proximal ledge 205.

The functionality of the superstructure attachment system will now be described. The dental implant connecting member 101 is tightly attached to the dental implant by a screw 109 threadably engageable with the dental implant. The main member 102a and the lever member 102b of the longitudinal member 102 are fitted to engage with partially spherically shaped distal end of the implant connecting member 101. As the lever member 102b and the main member 102a are in close contact along their longitudinal axis, the longitudinal member 102 may be angularly displaced relative the longitudinal axis of the implant connecting member 101 by means of the ball-socket joint formed at the interface between the implant connecting member 101 and the longitudinal member 102.

Then, casings 200 are inserted into pre-shaped cavities, corresponding to the outer shape of the casing 200, and adhered thereto through gluing or cementing. The casings 200 then receive the longitudinal members 102 in the cavities 201 thereof. The cavities of the casings 200 are shaped such that the proximal mouth for receiving the longitudinal member comprises a seat, in form of the ledge 205, for the flange 107 in a proximal zone of the longitudinal member 102. The cooperation between the flange 107 and the corresponding ledge 205 of the casing 200 will enhance the leverage of the separation force from separation of the main member 102a and the lever member 102b, since a distinct leverage/pivot point will be formed at the interface between the two.

When the casings 200 have been slid onto the longitudinal portion and the longitudinal member 102 consequently is positioned at a desired angle, the screw inserted into the screw bore 103 of the main member 102a is tightened such that it protrudes outside the main member 102a and consequently causing a relative movement between the lever member 102b and the main member 102a. As a distance between the lever member 102b and the main member 102a is induced, the partially spherically shaped recess 104a, 104b of the longitudinal member 102 will consequently clamp longitudinal member 102 to the implant connecting member 101, such that the longitudinal member 102 is tightly connected to the implant connecting member.

A superstructure may be attached to the system after the position of the longitudinal member 102 relative the implant connecting member 101 has been secured. Preferably, the superstructure comprises at least one interior channel for receiving the casings 200, and thereby also the longitudinal members 102. More preferably, each one of the interior channels is reachable from the oral cavity by an opening, such that the superstructure may be further attached to the system by means of a screw. Hence, the opening is aligned with the through hole 207 of the casings 200 and the screw hole 103 of the main member 102a of the longitudinal member 102.

The dental implant connecting member 101 is preferably a two-part piece, comprising a bolt and a fitting. The bolt has a threaded part 109 and tool receiving part 108 such that it may be tightly screwed into the implant. Before the bolt is fitted into the implant, it is inserted into the fitting such that the fitting will be secured relative the implant upon tightening of the bolt. For this purpose, the fitting is equipped with a protrusion 112 and a recess 111 which engage with the implant and/or the bone of the patient for preventing rotational movement of the fitting relative the implant.

The tool receiving part 108 is formed as a cylindrical or conical recess in the spherically shaped distal end, wherein the longitudinal axis of said recess is aligned with the longitudinal axis of the implant. Hence, the distal end is formed as a sphere integrally formed with the protrusion/recess part 111, 112, with a bore extending from the upper end through the sphere.

With reference to FIG. 2, the longitudinal member 102 will be described in more detail. Here, the longitudinal member 102 is formed by the main member 102a and the lever member 102b. When the lever member 102b is in close contact with the main member 102a, the longitudinal member is generally extending in a longitudinal direction and consists of three general parts; a cylindrical part, a flange, and a conical part. The cylindrical part is arranged at the distal end of the longitudinal member 102 and extends distally from the flange 107. Proximally of said flange 107, a conical part is arranged. The conical part comprises a proximal recess having a curvature corresponding to the distal end of the implant connecting member 101. The casing 200 is accordingly provided with a cavity 201 corresponding to longitudinal member 102, such that the longitudinal member 102 may be slid into the casing 200.

The main member 102a and the lever member 102b are facing each other via the surfaces 105a, 105b, which form a longitudinal interface between the lever member 102b and the main member 102a. The distal portion of the interface between the surfaces 105a, 105b is preferably substantially aligned with the longitudinal axis of the longitudinal member 102, while the proximal portion of the interface between the surfaces 105a, 105b is preferably angled relative the longitudinal axis of the longitudinal member 102, such that the interface surface 105a has a normal facing proximally and transversally and the interface surface 105b faces distally and transversally, with respect to the longitudinal direction of the member 102. In this way, the demounting of the casings 200, and thus the superstructure, from the implant connecting members 101, and thus the implant, may be facilitated, since the superstructure may be lifted in the distal direction once the screw member in screw hole 103 stops to exert pressure on the lever member 102b. In this position the superstructure may be lifted together with the main member 102a, due to the angled arrangement of the interface surfaces 105a, 105b in relation to the central axis of the longitudinal member 102. Hence, this arrangement of an at least partially angled interface area facilitates separation of the main member 102a and the lever member 102b by means of reducing the risk of that the members are stuck to each other. In other embodiments, the angled interface portion is made longer; e.g., the entire interface area may be angled relative the longitudinal axis of the longitudinal member 102. The interface area formed by the surfaces 105a, 105b, when viewed from above, may also be planar or curved.

Preferably, the interface between the surfaces 105a, 105b is ending at a position being located at the center of the spherical recess 104a, 104b of the proximal end of the longitudinal member 102. In other embodiments, however, the interface end point could be located slightly off-center.

As shown in FIG. 2, the through hole 103a of the main member 102a is substantially perpendicular to the longitudinal axis of the main member 102a. The lever member 102b has a corresponding seat 103b for receiving a screw protruding through said main member 102a.

In other embodiments, the screw hole 103a, 103b may be arranged differently and the engaging screw members may then be correspondingly adapted. For example, the screw hole 103a, 103b may extend through both the portions 102a, 102b, but the screw hole part corresponding to portion 102a having opposite threading direction than the threading direction in the screw hole part corresponding to portion 102b. Analogously, the screw member may have the corresponding threads, such that screwing action on the screw member in the screw hole 103 will result in increased separation effect. One rotation of the screw member will then result in a separation of the portions 102a, 102b corresponding to two thread heights.

In further embodiments, the threaded holes 103a, 103b may be arranged at a different angle such that the mouth of the through hole 103a is directed slightly distally.

The diameter of the longitudinal member 102 is preferably in the range of 2 to 5 mm, such that it may be accommodated within the oral cavity while still providing sufficient strength and stability to the casing 200, and thus the superstructure. The total length of the longitudinal member is in the range of 10 to 15 mm, and hence the displacement of the lever member 102b relative the main member 102a is sub-millimeter at the most distal end in order to provide sufficient clamping of the longitudinal member 102 to the implant connecting member 101. Accordingly, the cavity 201 of the casing 200 is adapted to snuggly receive a longitudinal member 102 in a sliding manner.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dental superstructure attaching system for use with a dental implant, said dental superstructure attaching system comprising:
(i) a longitudinal member being connectable with an implant or an implant connecting member via an at least partially curved interface area at a proximal end of said longitudinal member, said longitudinal member comprising
a main member; and
a lever member;
wherein said longitudinal member further comprises means for urging said lever member and said main member away from each other, such that said longitudinal member is secured to said implant or implant connecting member; and
(ii) a casing for attachment to a dental superstructure on an outer surface of the casing, said casing comprising
a cavity for housing the longitudinal member, such that when urging said lever member and said main member away from each other, the longitudinal member is secured in said cavity; and
(iii) wherein said means for urging said lever member and said main member away from each other comprises a screw inserted into a threaded through hole of said main member and engaging with said threads of said through hole such that the screw protrudes outside the main member and pushes the lever member away from said main member, and said casing having a through hole in a side wall thereof, said through hole in the side wall communicating with said cavity and corresponding in position to the through hole of said main member.

2. The system of claim 1, further comprising an implant connecting member, and wherein the proximal end of said longitudinal member comprises a partially spherically shaped recess, and wherein a distal end of said implant connecting member comprises a partially spherically shaped protrusion.

3. The system of claim 1, wherein the longitudinal member has a circular cross-section.

4. The system according to claim 3, wherein the longitudinal member comprises a flange arranged between the proximal end and a distal end of said longitudinal member, and wherein the casing comprises a ledge at a proximal end opening of said cavity, corresponding to said flange, such that a pivot point for said lever member is formed at an interaction surface between the flange and the ledge.

5. The system according to claim 1, wherein a first portion of a longitudinal interface between the main member and the lever member is angled relative a longitudinal axis of the longitudinal member.

6. The system according to claim 5, wherein a second portion of the longitudinal interface between the main member and the lever member is parallel to the longitudinal axis of the longitudinal member.

7. The system according to claim 1, wherein said lever member comprises a threaded recess axially aligned with the through hole of the main member, such that said recess and said through hole are configured to receive the screw.

8. The system according to claim 7, wherein said screw is configured to connect the main member with the lever member while at the same time allowing relative movement of the main member and the lever member.

9. The system according to claim 8, wherein the threads of the through hole are in opposite direction than the threads of the recess.

* * * * *